United States Patent [19]

Hughes

[11] 4,378,385

[45] Mar. 29, 1983

[54] METHOD OF MAKING OXYGEN ION CONDUCTING SOLID ELECTROLYTE DEVICE

[75] Inventor: Antony E. Hughes, Didcot, England

[73] Assignee: United Kingdom Atomic Energy Authority, London, England

[21] Appl. No.: 244,256

[22] Filed: Mar. 16, 1981

[30] Foreign Application Priority Data

Mar. 28, 1980 [GB] United Kingdom ............. 80 10558

[51] Int. Cl.³ .................... B05D 5/12; G01N 27/00
[52] U.S. Cl. ................. 427/126.3; 427/126.1; 427/58; 427/376.2; 427/430.1; 427/443.1
[58] Field of Search ............... 427/126.3, 58, 430.1, 427/443.2, 376.2, 126.1; 252/62.2, 317; 204/195 S

[56] References Cited

U.S. PATENT DOCUMENTS

| | | | |
|---|---|---|---|
| 2,914,808 | 12/1959 | Adams | 264/215 |
| 4,126,532 | 11/1978 | Takao et al. | 204/195 S |
| 4,181,593 | 1/1980 | McKinzie et al. | 427/126.3 |
| 4,206,169 | 6/1980 | Hall | 427/435 |
| 4,220,678 | 9/1980 | Feldstein | 427/305 |
| 4,242,191 | 12/1980 | Schindler et al. | 427/77 |
| 4,244,986 | 1/1981 | Paruso et al. | 427/126.4 |

FOREIGN PATENT DOCUMENTS

| | | |
|---|---|---|
| 1042589 | 7/1966 | United Kingdom . |
| 1231280 | 5/1971 | United Kingdom . |
| 1362184 | 7/1974 | United Kingdom . |
| 1386244 | 5/1975 | United Kingdom . |
| 1456885 | 1/1976 | United Kingdom . |
| 1470482 | 4/1977 | United Kingdom . |
| 1479275 | 7/1977 | United Kingdom . |
| 1479401 | 7/1977 | United Kingdom . |
| 1556944 | 11/1979 | United Kingdom . |

*Primary Examiner*—Michael R. Lusignan
*Assistant Examiner*—Richard Bueker
*Attorney, Agent, or Firm*—Larson and Taylor

[57] ABSTRACT

The present invention relates to electrical devices and to the preparation thereof.

According to one aspect of the present invention there is provided an electrical device having a portion comprising an oxygen ion conducting solid electrolyte wherein the portion comprising an oxygen ion conducting solid electrolyte has been formed by a method including deposition onto a substrate from a solution or dispersion.

There is also disclosed a method for the preparation of an electrical device in accordance with the present invention.

5 Claims, 3 Drawing Figures

METHOD OF MAKING OXYGEN ION CONDUCTING SOLID ELECTROLYTE DEVICE

The present invention relates to electrical devices and to the preparation thereof.

According to one aspect of the present invention there is provided an electrical device having a portion possessing selected electrical properties wherein the portion possessing selected electrical properties has been formed by a method including deposition onto a substrate from a solution or dispersion.

According to another aspect of the present invention there is provided a method for the preparation of an electrical device having a portion possessing selected electrical properties which includes forming the portion possessing selected electrical properties, or a precursor therefor, by deposition onto a substrate from a solution or a dispersion.

The portion possessing selected electrical properties can be, for example, an ion-permeable portion, or an insulating portion, or a semi-conducting portion.

The term "ion-permeable" as used in this specification means capable of permitting the passage of ions (e.g. by ion conduction or otherwise).

The term "solution" as used herein means true solution. The term "dispersion" as used herein embraces a colloidal dispersion, a suspension and a slurry.

In one embodiment the dispersion may be a colloidal solution (i.e. a sol).

In another embodiment the dispersion may contain a colloidal component (or components) and one (or more) other component(s) (e.g. a dispersion may comprise a sol and a metal salt present in solution).

Where the dispersion is a colloidal solution or is a dispersion having a colloidal component (or components) and one (or more) other component(s) the portion of the electrical device possessing selected electrical properties may be formed from the dispersion by effecting a sol-gel transformation and subsequently heating the gel thereby formed if such heating is necessary.

The sol-gel transformation may be effected by any suitable technique. Such techniques include water removal and anion extraction which are known in the art.

It is preferred that the portion of the electrical device possessing selected electrical properties is formed as a layer on another material (i.e. a substrate). "Layer" as used herein embraces "film" and "coating".

Thus, for example, an ion-permeable layer can be provided in accordance with the present invention to act as an electrolyte layer, or as a protective coating which permits the passage of selected ions.

A layer possessing selected electrical properties may be formed on a substrate in accordance with one embodiment of the present invention by dipping the substrate into the solution or dispersion, thereby to coat the substrate with solution or dispersion, and converting the solution or dispersion to the layer.

In another embodiment a layer possessing selected electrical properties may be formed on a substrate by applying the solution or dispersion to a selected area of a substrate and converting the solution or dispersion to the layer.

The solution or dispersion may be applied by any suitable technique for example, "painting", thick film processes or doctor blading.

In the case of using a dispersion which is a colloidal solution or has a colloidal component in accordance with the two immediately preceding embodiments of the invention the dispersion on the substrate may be treated to effect a sol-gel transformation (e.g. by drying) to give a solid layer on the substrate. This layer may be subsequently heat treated to produce a layer possessing selected electrical properties (e.g. a ceramic layer).

The present invention has wide flexibility with regard to the nature of the portion of the device possessing selected electrical properties since the solution or dispersion can be selected from a wide range. For example, many chemical compounds can be obtained in colloidal solution or in a dispersion having a colloidal component (or components).

Thus, by way of example, insulating portions can be prepared from colloidal solutions or dispersions having a colloidal component (or components) from which an insulating oxide (e.g. $Al_2O_3$ or $SiO_2$) can be formed.

Similarly, by way of example, an ion-permeable portion (e.g. an electrolyte) can be prepared from (i) a colloidal solution, or a dispersion having a colloidal component (or components), from which ion conducting oxide electrolytes can be formed (e.g. $ZrO_2$ or $CeO_2$ doped with divalent or trivalent ions such as $Ca^{2+}$ or $Y^{3+}$) or (ii) a colloidal solution, or a dispersion having a colloidal component (or components), from which alkali ionic conducting electrolytes can be formed (e.g. $Na\beta Al_2O_3$ or $Na_{1+x}Zr_2Si_xP_{3-x}O_{12}$ (i.e. "NASICON")).

Colloidal solutions (i.e. sols) which may be used in accordance with the present invention include, for example, ceria sols such as the ceria sol disclosed at page 3 line 49 of British Patent Specification No. 1342893 (UKAEA), zirconia sols such as the zirconia sol disclosed in British Patent Specification No. 1181 794, a $TiO_2$ as disclosed in British Patent Specification No. 1412937, and a $SiO_2$ sol believed to be made by hydrolysing sodium silicate and commercially available from Mansanto under the trade name "Syton".

It is to be noted, by way of example, that British Patent Specification No. 1386 244 (UKAEA) discloses, inter alia, the preparation of $\beta$-alumina from a sol (i.e. colloidal solution) and that British Patent Application No. 7920506 (UKAEA) (now published as U.K. Patent Application 2052462) discloses a process for use in the preparation of a material of the general formula $Na_{1+x}Zr_2Si_x P_{3-x}O_{12}$ (NASICON).

Other dispersions, comprising a colloidal solution or a dispersion having a colloidal component (or components) and one (or more) other component(s) may be used in accordance with the present invention to provide in an electrical device a portion (e.g. a layer) possessing selected electrical properties.

Thus, appropriate dispersions can be used in accordance with the present invention to provide in an electrical device portions possessing semi-conducting properties (e.g. $TiO_{2-x}$ and $In_2O_3:SnO_2$), or high dielectric constant properties (e.g. $TiO_2$ and $CaTiO_3$) or ferroelectric properties (e.g. $PbTi_{1-x}Zr_xO_3$), or ferrimagnetic properties (e.g. Sr Ferrites).

It is to be noted, by way of example, that British Patent Specification No. 135 1113 (UKAEA) discloses, inter alia, the preparation of an indium oxide gel from a sol (i.e. colloidal solution) and that also (British Patent Specification No. 1266494 (UKAEA) discloses, inter alia, a process for the formation of mixed oxide compounds (e.g. ferrites) from a solution).

In applications where it is desired to produce a layer possessing selected electrical properties (e.g. in producing electrolyte layers) it is generally preferred to choose a dispersion which is a colloidal solution, or a dispersion having a colloidal component (or components) and one other component(s), such that a dense layer is produced (i.e. a layer of low porosity) on effecting a sol-gel transformation. For example using a ceria sol as disclosed above a density of ~98% TD may be achieved in a layer typically about 1 $\mu$m or a few microns in thickness.

Where a particular application requires porosity in a layer the dispersion may be selected accordingly.

Thus, by way of example, a dispersion comprising or containing a sol formed by dispersing a powder produced by a vapour phase condensation process (e.g. flame hydrolysis) in water may be used to introduce porosity into a layer. British Patent Application No. 43463/75 (UKAEA) (now BP 1567003) describes, inter alia, the production of sols from a commercially available powder produced by flame hydrolysis.

In addition to the choice of dispersion the porosity and density of a layer may be influenced by the method of coating, the method used in effecting a sol-gel transformation and any subsequent processing steps (e.g. the firing of a gel layer to give a ceramic layer).

In electrical devices using a solid electrolyte such as selective ion monitors, batteries and fuel cells, there can be benefits to be gained if the electrolyte is as thin as practically possible.

This arises mainly because in devices which draw significant current the internal resistance is proportional to the thickness of the electrolyte.

In known electrical devices electrolyte layers of about 1 mm thickness are used. The present invention can be utilised to produce significantly thinner (e.g. about 1 $\mu$m to a few microns) electrolyte layers in electrical devices, thereby to offer reduced internal resistance. United Kingdom Atomic Energy Authority Patent Application No. PCT/GB78/00029 made under the Patent Co-operation Treaty and having the International Publication No. WO79/00247 discloses an invention relating to providing substrates with coatings obtainable from sols.

As hereinbefore disclosed the present invention has wide flexibility with regard to the nature of the portion of the device possessing selected electrical properties since the solution or dispersion can be selected from a wide range.

Thus, for example, the present invention finds application in relation to a wide range of electrical devices and uses of which the following are examples:

(i) Nerstian sensors for the measurement or detection of, for example, oxygen or oxidizing gases. (A layer of electrolyte may be provided in accordance with the present invention).

(ii) Gas sensors utilising semi-conducting materials (e.g. using a layer of semi-conducting oxide produced in accordance with the present invention).

(iii) Gas sensors utilising catalytic or porous coatings provided in accordance with the present invention.

(iv) Devices in which a thin film of oxide is used on a semi-conductor such as silicon either to produce particular electrical behaviour (e.g. as an MOS transistor) or to make a sensor device in which the electrical properties of the semi-conductor-oxide structure are used to sense changes in the environment of the device.

(v) Batteries or fuel cells having thin layers of solid electrolytes provided in accordance with the present invention.

(vi) Thin conducting coatings or transparent coatings to provide electrical conduction on the surface of materials, for example, as electrodes or connectors for electro-optic displays or as coatings to prevent charging of optical surfaces or surfaces used for thermal control of devices e.g. in space satellites.

(vii) Thin semi-conductors (e.g. oxides) in photovoltaic or photoelectrolysis devices.

(viii) Protective or encapsulating coatings for semi-conductor or other electrical devices.

(ix) Thin film piezoelectric or pyroelectric devices (e.g. transducers and radiation detectors).

(xi) Thin film magnetic devices (e.g. for memory devices).

In a further embodiment of the invention the portion may be removed from the substrate after formation and subsequently incorporated in an electrical device. Thus, for example, a layer can be deposited on a substrate and subsequently removed and used in an electrical device. A shaped (e.g. thimble shaped) portion for incorporation in an electrical device may be formed by deposition onto a suitably shaped substrate and subsequent removal therefrom.

BRIEF DESCRIPTION OF THE DRAWINGS

The invention will now be further described, by way of example only, with reference to the accompanying drawings in which.

Referring now to FIG. 1 of the drawings there is shown a tube 1 (e.g. of metal or ceramic material) closed at one end by a porous plug 2. (The porous plug 2 may be a porous type of the material of the tube 1. For example if the tube 1 is of nickel the plug 2 can be of porous nickel). The porosity of plug 2 is such that, in operation, a reference gas of fixed oxygen partial pressure ($p_{ref}$) can permeate therethrough. A layer of solid electrolyte 3 is provided on the plug 2 and is partially overlaid by a sensing electrode 4 (e.g. a platinum electrode). Electrical connections 5 and 6 are provided to connect respectively the porous plug 2 and sensing electrode 4 to a millivoltmeter (not shown).

Figure 1:
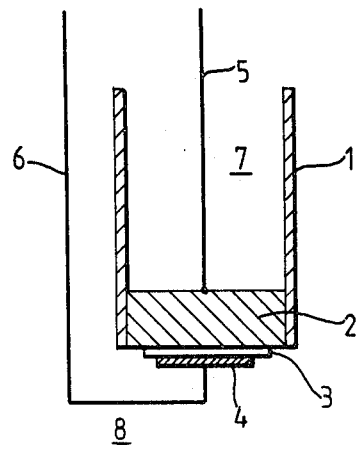
FIGS. 1, 2 and 3 are diagrammatic representations of electrical devices having portions possessing selected electrical properties in accordance with the present invention. The electrical devices shown are oxygen sensors and a portion possessing selected electrical properties in each case is a layer of solid electrolyte.

Plug 2 is made of a substance capable, in operation, of catalysing the reference electrode reaction $\frac{1}{2}O_2 + 2e \rightarrow O^{2-}$.

In operation a reference gas of fixed oxygen partial pressure ($P_{ref}$) is maintained in region 7 and a fluid, the oxygen partial pressure (p) of which is to be measured, is provided in region 8.

The Nernst voltage (V) between the plug 2 and electrode 4 measured by the millivoltmeter (not shown) can be used to calculate the oxygen partial pressure in the region 8 by the relationship:

$$V = \frac{RT}{4F} \ln (P\,ref/p)$$

(It is to be noted that plug 2 may optionally be made of a substance which does not catalyse the reference electrode reaction. In this case a suitable catalysing electrode capable of catalysing the reaction (e.g. porous Pt) is provided between plug 2 and the electrolyte 3 and the connection 5 is used to connect the catalysing electrode to the millivoltmeter (not shown)).

The layer of solid electrolyte 3 is provided on the plug 2 by applying a dispersion of an appropriate composition to the plug 2 and subsequently effecting a sol-gel transformation and thereafter heating to form a ceramic layer.

The sensing electrode 4 (e.g. Pt) may be provided by deposition, e.g. from a suitable dispersion.

Figure 2:
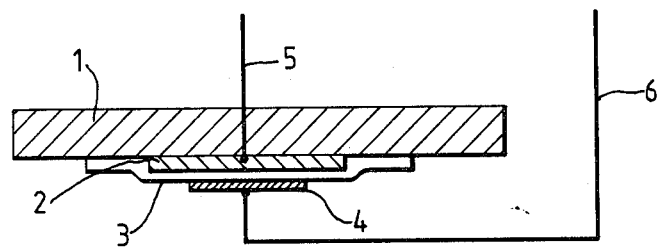

Referring now to FIG. 2 of the drawing there is shown a inert substrate 1 carrying a metal/metal oxide reference electrode 2. A layer of solid electrolyte 3 is provided over the electrode 2 and a sensing electrode 4 is provided partially overlaying the electrolyte 3. Electrical connections 5 and 6 are provided to connected respectively the reference electrode 2 and the sensing electrode 4 to a millivoltmeter (not shown).

In operation a fluid the oxygen partial pressure of which is to be measured is provided in region 7.

The Nernst voltage (V) measured by the multivoltmeter (not shown) can be used to calculate the oxygen partial pressure in the region 7 as hereinbefore disclosed in relation to FIG. 1.

The layer of solid electrolyte 3 (and the sensing electrode 4 if desired) may be provided as hereinbefore disclosed in relation to FIG. 1.

Figure 3:
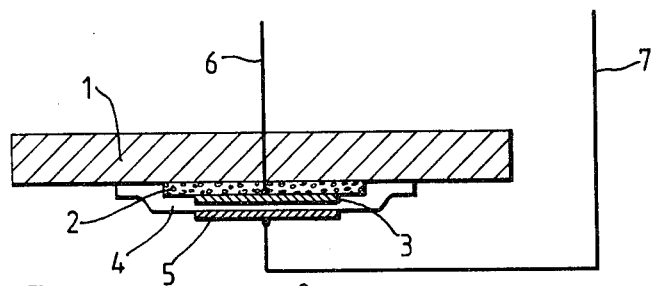

Referring now to FIG. 3 of the drawings there is shown an inert substrate 1 carrying a porous material 2 in which is trapped oxygen or an oxygen containing gas. The material 2 is provided with an electrode 3 (e.g. of Pt) and both are overlaid with a layer of solid electrolyte 4.

A sensing electrode 5 partially overlays the solid electrolyte 4 and electrical connections 6 and 7 connect, respectively the electrode 3 and sensing electrode 5 to a millivoltmeter (not shown).

In operation a fluid the oxygen partial pressure of which is to be measured is provided in region 8.

The Nernst voltage measured by the millivoltmeter (not shown) can be used to calculate the oxygen partial pressure in region 8 as hereinbefore disclosed in relation to FIG. 1. (It will be appreciated that the material 2 (containing oxygen or an oxygen containing gas) and the electrode 3 constitute a reference electrode).

The layer of solid electrolyte 4 (and in the electrodes 3 and 5 is desired) may be provided as hereinbefore disclosed in relation to FIG. 1.

I claim:

1. A method for the preparation of an electrical sensor device having a portion comprising an oxygen ion conducting solid electrolyte, which method comprises forming the electrolyte by deposition onto a substrate from a colloidal dispersion of an inorganic material, said colloidal dispersion comprising a colloidal solution, or a dispersion having a colloidal component, from which oxygen ion conducting electrolyte can be formed.

2. A method as claimed in claim 1 wherein the colloidal dispersion contains a colloidal component and another component.

3. A method as claimed in claim 1 wherein the electrolyte is formed from the colloidal dispersion by effecting a sol-gel transformation to form a gel and heating the gel.

4. A method as claimed in claim 1 wherein said portion of electrolyte is formed as a layer on a substrate by dipping the substrate into the colloidal dispersion, thereby to coat the substrate with dispersion, and converting the dispersion to a layer.

5. A method as claimed in claim 1 wherein said portion of electrolyte is formed as a layer on a substrate by applying the colloidal dispersion to a selected area of the substrate and converting the dispersion to a layer.

* * * * *